(12) United States Patent
Hasegawa

(10) Patent No.: US 7,267,648 B2
(45) Date of Patent: Sep. 11, 2007

(54) MAGNIFYING IMAGE PICKUP UNIT FOR AN ENDOSCOPE, AN ENDOSCOPE FOR IN VIVO CELLULAR OBSERVATION THAT USES IT, AND ENDOSCOPIC, IN VIVO CELLULAR OBSERVATION METHODS

(75) Inventor: Naoki Hasegawa, Chofu (JP)

(73) Assignee: Olympus Corporation, Tokyo (JP)

( * ) Notice: Subject to any disclaimer, the term of this patent is extended or adjusted under 35 U.S.C. 154(b) by 140 days.

(21) Appl. No.: 10/808,309

(22) Filed: Mar. 25, 2004

(65) Prior Publication Data
US 2004/0210113 A1 Oct. 21, 2004

(30) Foreign Application Priority Data
Mar. 31, 2003 (JP) .............................. 2003-094028

(51) Int. Cl.
*A61B 1/06* (2006.01)
(52) U.S. Cl. ...................................................... 600/168
(58) Field of Classification Search ................ 600/160, 600/168, 177–178, 180, 476, 478
See application file for complete search history.

(56) References Cited

U.S. PATENT DOCUMENTS 3,889,662 A * 6/1975 Mitsui ........................ 600/139
2003/0176768 A1* 9/2003 Gono et al. .................. 600/109
2004/0092829 A1* 5/2004 Furnish et al. ............... 600/478
2004/0097791 A1* 5/2004 Tokuda et al. ............... 600/173
2004/0111031 A1* 6/2004 Alfano et al. ................ 600/476
2004/0186363 A1* 9/2004 Smit et al. ................... 600/317

* cited by examiner

*Primary Examiner*—John P. Leubecker
*Assistant Examiner*—Philip R Smith
(74) *Attorney, Agent, or Firm*—Arnold International; Bruce Y. Arnold

(57) ABSTRACT

An endoscope observation system for in vivo cellular observation is disclosed that includes an illumination optical system having a light source for supplying illumination light to an object, an objective optical system that forms a magnified image of the object such that the absolute value of the image scale factor exceeds unity, and an image pickup unit that detects the magnified image. The illumination optical system is provided with a wavelength selection means for dividing, among the blue, green, and red wavelength ranges in the illumination light from the light source, either the blue wavelength range or the red wavelength range into two wavelength bands T1 and T2, with the wavelength band T1 being nearer the green wavelength range than is the wavelength band T2, and light in the wavelength band T1 is prevented from illuminating the object. An in vivo cellular observation method is also disclosed using an endoscope.

11 Claims, 12 Drawing Sheets

MAGNIFYING IMAGE PICKUP UNIT FOR AN ENDOSCOPE, AN ENDOSCOPE FOR IN VIVO CELLULAR OBSERVATION THAT USES IT, AND ENDOSCOPIC, IN VIVO CELLULAR OBSERVATION METHODS

This application claims the benefit of foreign priority from Japanese Patent Application No. 2003-094028, filed Mar. 31, 2003, the contents of which are hereby incorporated by reference.

BACKGROUND OF THE INVENTION

Conventional endoscopes have a large field of view that is in the range of about 90° to 140° so that tissues inside a body can be observed without overlooking lesions. They also change the distance to the object in order to obtain either magnified or reduced-sized images of an object to be observed, and thus have a large depth of field for a fixed focus point so that objects at distances between 3 mm and 50 mm can be observed without refocusing.

Conventional endoscopes also have an image scale factor with an absolute value of about 30 to 50 when the image is displayed on a monitor having a 14-inch screen, which is sufficient to observe diseased tissues. Zoom optical systems are used in order to obtain further magnified images, with the absolute value of the image scale factor being approximately 70 when displayed oil a monitor having a 14-inch screen. The zoom optical system typically has a built-in, zoom lens driving mechanism. As a result, the endoscope has an insert tip with an outer diameter that is larger than 10 mm and requires complex operations. Such endoscopes have limited applications.

The manner in which living tissues are observed using a conventional endoscope will now be described with reference to FIG. 1. Living tissues to be observed by a conventional endoscope often include a mucous membrane 1, transparent epithelial cells 2 and underlying parenchymal tissues 3 in which blood vessels run. Light illumination emitted at the endoscope tip part 4 must first pass through the mucous membrane and the transparent epithelial cells before reaching the parenchymal tissues. The illumination light which reaches the parenchymal tissues 3 is scattered by the parenchymal tissues 3. Of the light that is scattered by the parenchymal tissues, most re-enters the epithelial cells. The illumination light is also scattered by cell walls 5 and cell nuclei 6 when it is transmitted through the transparent epithelial cells. The light rays B1, B2 that are scattered by the cell nuclei of the epithelial cells are weak and thus the light rays that are scattered by the parenchymal tissues dominate. Consequently, in a conventional endoscope, only the parenchymal tissues are observed through an objective optical system.

When it becomes difficult to provide a diagnosis of an abnormality by observing images of a tissue, such as when a lesion is very small, a suspicious-looking tissue may be excised during the course of an endoscopic examination. The cells of the excised tissue are then examined under a microscope. Whereas an endoscope generally uses incident illumination from an illumination optical system that is positioned around an objective optical system, a microscope instead generally uses an objective optical system and an illumination optical system that are positioned on opposite sides of a sample. The sample is normally pre-processed in order to make it more suitable for observation, such as by removing the parenchymal tissues by slicing the sample thin in order to reduce scattering and/or by staining the sample in order provide better contrast.

The manner in which a sample is observed using a microscope will now be described with reference to FIG. 2. A prepared sample is fixed onto a cover glass 7 and illuminated from below with light from an illumination system 8. Illumination light rays A1', A2' are diffracted by the cell walls and cell nuclei as they transmit through the sample 9. The diffracted light rays B1', B2' interfere with one another both constructively and destructively, producing interference fringes that provide visible contrast. Thus, one can observe the sample by using an objective optical system 10 placed above the sample.

Laser-scanning-type confocal endoscopes which have a resolution sufficient for cellular observation have been proposed that may be inserted within a living body. These typically use a confocal optical system having a pinhole for passing an Airy disk light pattern at a position that is conjugate to the image plane, and the confocal optical system thus acquires diffraction-limited information for each point of an object in the field of view. A laser beam directed from a light emitting optical system scans the object, and information obtained from the reflected light from the object for each point is combined so as to produce an image representing either a two-dimensional or a three-dimensional object. High resolution can thus be realized not only within the image plane, but also in the depth direction.

It takes from several days to several weeks to identify abnormal tissue using conventional procedures wherein living tissues are excised and examined in vitro. Moreover, a cellular sample that is isolated and fixed for observation is only a tiny part of a removed tissue. Thus, although a cellular sample provides information on cellular structures, it is incapable of providing important functional information, such as information concerning fluid circulation within cells. This is because the circumstances between in vitro and in vivo examination are completely different. Thus, there is a need for magnifying endoscopes that will provide real-time, in-vivo observation of intact living cells.

In order to form cellular images of a lesion within a living body, a small-sized image pickup unit is necessary that is provided with an objective optical system with an image scale factor having an absolute value that is nearly as high as that of a microscope and which provides high resolution. The objective optical system used in a conventional endoscope does not meet these requirements. As mentioned previously, in a conventional endoscope as shown in FIG. 1, the illumination light is diffracted by the cell walls and cell nuclei as it transmits through the epithelial cells. The diffracted light rays B1, B2 are weak and the light rays A1, A2 that are scattered by the parenchymal tissues are dominant. Consequently, using a convention endoscope, only data from the parenchymal tissues is imaged by the objective optical system.

Although a conventional objective optical system as used in microscopes is satisfactory as far as providing sufficient imaging performance, such an objective optical system is too large for easy insertion into a living body. Laser-scanning-type confocal endoscopes have a problem in that their scanning speeds are still too slow for real-time, in vivo observations. Thus, as described above, an image pickup unit that meets the requirements for in vivo cellular observation has not yet been realized.

BRIEF SUMMARY OF THE INVENTION

The present invention relates to a magnifying image pickup unit suitable for in vivo cellular observation, an endoscope for in vivo cellular observation, and an in vivo cellular observation method.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

Figure 1:
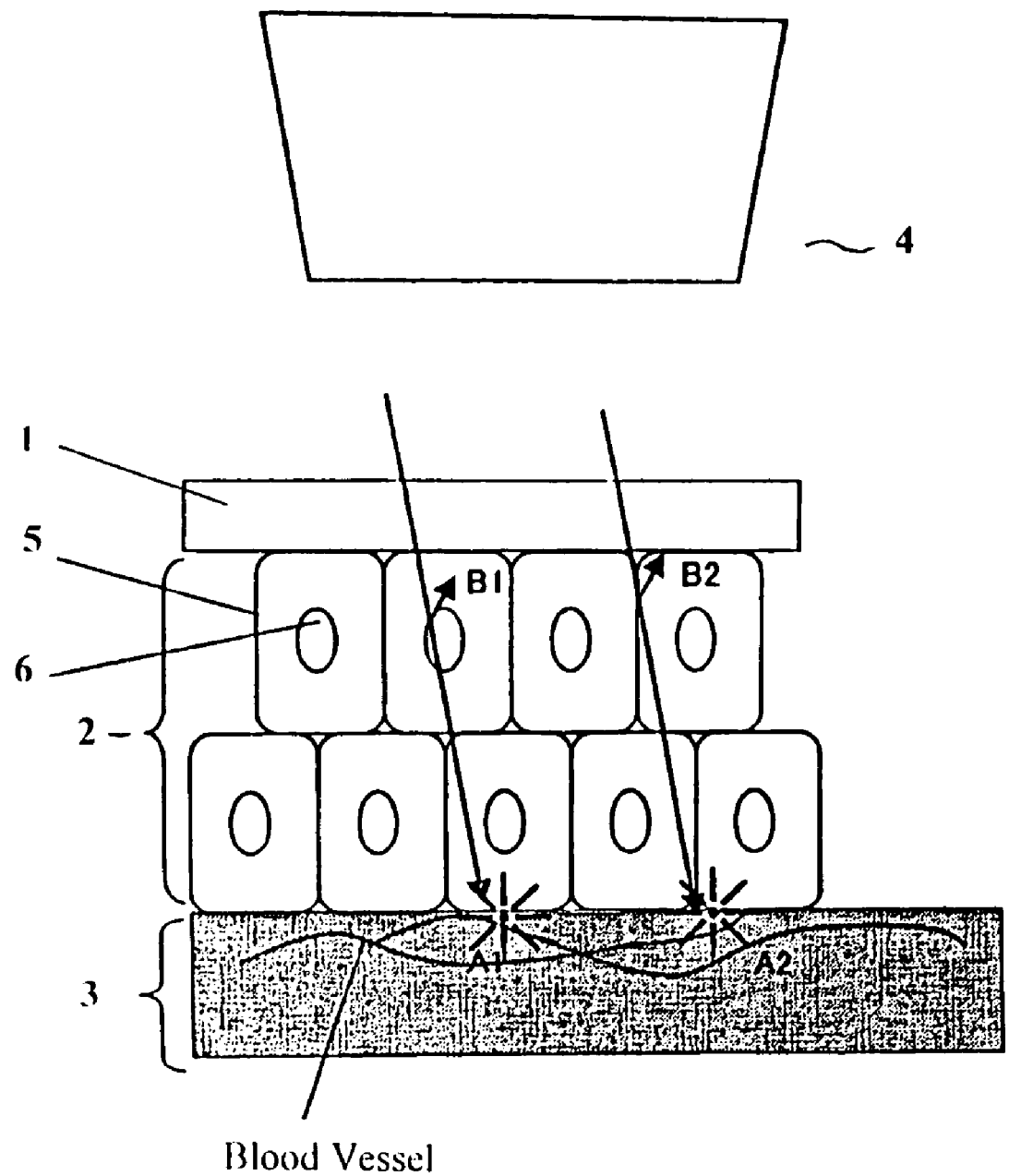
FIG. 1 is an illustration to explain a principle of living tissue observation using a prior art endoscope.
Figure 2:
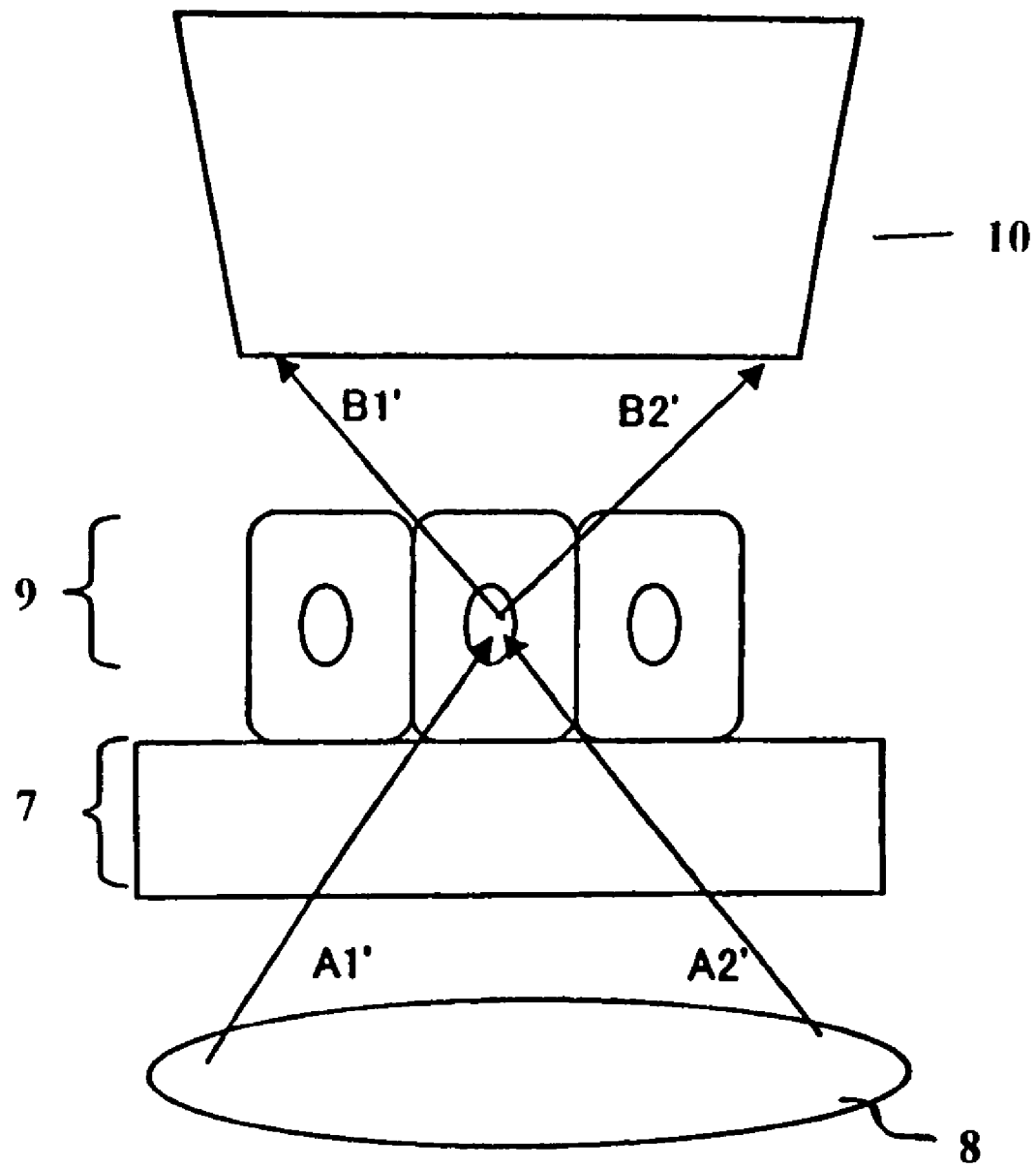
FIG. 2 is an illustration to explain a principle of excised sample observation using a microscope.

A magnifying image pickup unit according to the present invention that is applied to an endoscope for use in in vivo cellular observation will now be described.

First, a conventional endoscope having a wide-angle field of view is used so as to provide a thorough examination of tissues in an area of the body without overlooking any area that may contain diseased tissue. Because it is difficult to diagnose a region of tissue using images observed with a conventional endoscope, an endoscope to which the magnifying image pickup unit of the present invention is applied (hereinafter termed a magnifying endoscope) is used to cellularly examine a region of tissue.

For magnified cellular observation, coloring agents generally will have been previously delivered to the area, if necessary. Within a certain time period after the coloring agent is delivered, the difference in the time required for the cell nuclei, the cell walls, and the other cell components to excrete the coloring agent creates contrast in the object. Then, a magnifying endoscope is guided to the region and contact is made with the object at the tip of the magnifying endoscope while observations using a conventional endoscope are continued. Preferably, a tissue image from a conventional endoscope and a cellular image from a magnifying endoscope are displayed simultaneously on a TV monitor. In this way, the magnifying endoscope can be guided precisely to a very small, targeted region within an extensive observation field of view in order to magnify and observe cell nuclei and cell walls.

Before providing a detailed explanation of a magnifying image pickup unit according to the present invention, the requirements for an image pickup unit that may be used in a magnifying endoscope will be discussed. First, the scale factor required for visualizing fine cellular structures will be discussed. The overall observation scale factor bm of an image observed on a display monitor is given by the following equation:

$$bm = |\beta o| \cdot bd \quad \text{Equation (A)}$$

where $\beta o$ is the image scale factor of the objective optical system, namely, the height of the image as formed on the image pickup element divided by the actual height of the object, and bd is the display scale factor, defined as the monitor display screen element size divided by the image pickup element size.

Conventional endoscopes realize an overall observation scale factor of about 30 to 50 when the images are viewed on a 14-inch display monitor. Zoom optical systems having a magnifying function realize an image scale factor with an absolute value of approximately 70. However, an overall observation scale factor in the range of approximately 200 to 2000 is necessary for cellular observation when viewed on a 14-inch monitor. Therefore, it is desired that the objective optical system satisfies the following conditions:

$$1 < |\beta o| \leq 10 \quad \text{Condition (1)}$$

$$0.9 \leq |\cos wy'/\cos wy| \leq 1.1 \quad \text{Condition (2)}$$

where $\beta o$ is the image scale factor of the objective optical system, wy' is the incident angle at which a chief ray corresponding to the largest field angle enters the image pickup surface, and wy is the half-field angle.

When the lower limit of Condition (2) is not satisfied, the incident angles of rays onto the image pickup element will be too large, failing to maintain uniform image qualities (for example, color reproducibility and brightness) within the field of view. When the upper limit of Condition (2) is not satisfied, the field angle will be too large, failing to ensure a required scale factor.

Image resolution will now be discussed. Diseased tissues can be identified with an image resolution in the range of millimeters and sub-millimeters. However, cellular observations require an image resolution in the range of microns and sub-microns. In order to form detailed images of an object that is both transparent and provides only a small difference in refractive indexes, the interference of diffracted light rays from the object may be used so as to provide images having enhanced contrast. The objective optical system needs to have a larger numerical aperture NA on the object side so as to collect higher orders of diffracted light rays and, preferably, satisfies the following Condition (3):

$$0.1 \leq NA \leq 0.8 \qquad \text{Condition (3)}$$

In the case where the cell walls are observed, it is preferable to satisfy the following Condition (3'):

$$0.3 \leq NA \leq 0.8 \qquad \text{Condition (3')}$$

In addition, in order to obtain both high contrast and high resolution imaging, the objective optical system should have a resolution higher than that determined by the pitch of the image pickup element, without exceeding the resolution determined by the diffraction limit. The objective optical system preferably satisfies the following Condition (4):

$$0.1 \leq |p \cdot NA^2/(0.61 \cdot \lambda \cdot \beta o)| \leq 0.8 \qquad \text{Condition (4)}$$

where p is the pixel size of the image pickup element,

NA is the numerical aperture of the objective optical system on the object side;

$\lambda$ is the e-line wavelength (i.e., $\lambda$=0.546 µm), and $\beta o$ is the image scale factor of the objective optical system.

When the lower limit of Condition (4) is not satisfied, sufficient contrast will not be obtained. When the upper limit of Condition (4) is not satisfied, aberrations become difficult to correct, resulting in the failure to obtain fine images.

Miniaturization (i.e., down-sizing) of the magnifying endoscope will now be discussed. It is desirable that the magnifying endoscope have an outer diameter $\Phi$ of less than 4 mm in order that it may be guided to an observation object through a treatment tool insert channel of a conventional endoscope. Accordingly, it is desirable that the objective optical system be miniaturized so as to have an outer diameter $\Phi$ of less than 2 mm.

A desired, small-sized, objective optical system having an image scale factor with a large absolute value and a high resolution comprises, in order from the object side: a lens unit having positive refractive power and an aperture stop, wherein the following Condition (5) is satisfied:

$$0.2 \leq \Phi 1/(\Phi 2 \cdot f1) \leq 2 \qquad \text{Condition (5)}$$

$\Phi 1$ is the diameter of the aperture stop, $\Phi 2$ is the largest outer diameter of the objective optical system, and f1 is the focal length of the lens unit having a positive refractive power.

Condition (5) prevents the objective optical system from having a larger diameter in association with a larger numerical aperture NA, thus facilitating miniaturization. When the lower limit of Condition (5) is not satisfied, the objective optical system will have a larger total length and a larger maximum diameter, hampering miniaturization. When the upper limit of Condition (5) is not satisfied, aberrations become difficult to correct.

In order to obtain a flat image surface, it is desirable that the objective optical system be formed of, in order from the object side, a front lens unit having positive refractive power, an aperture stop, and a rear lens unit having positive refractive power. In such a case, the following Condition (6) is preferably satisfied in order to achieve both miniaturization and an image scale factor having a large absolute value:

$$2 \leq f2/f1 \leq 10 \qquad \text{Condition (6)}$$

where f1 is the focal length of the front lens unit, and f2 is the focal length of the rear lens unit.

When the lower limit of Condition (6) is not satisfied, a required image scale factor having a large absolute value will not be maintained. When the upper limit of Condition (6) is not satisfied, a larger overall length and a larger maximum diameter of the objective optical system will hamper miniaturization.

Various embodiments of a magnifying image pickup unit of the present invention will now be described.

EMBODIMENT 1

The structure of Embodiment 1 of the magnifying image pickup unit will now be discussed with reference to FIGS. 11(a) and 11(b), which show a side cross section and an end view, respectively, of the magnifying image pickup unit according to this embodiment.

The objective unit comprises an objective lens unit 101 having a uniform diameter in an objective frame 102. The objective lens unit 101 consists of, in order from the object side: a first lens group G1 having positive refractive power, an aperture stop 103, and a second lens group G2 having positive refractive power. An image pickup element 105 is affixed to an image pickup frame 106 via a cover glass 104, thereby forming an image sensor unit.

The image pickup unit is focused by changing the distance 107 between the objective lens unit and the image sensor unit. An insert section for a magnifying endoscope is constructed of a hard tip member 108 and an outer sheath member 110. The image pickup unit is affixed to the insert section via an intermediate member 109.

Figure 11A:
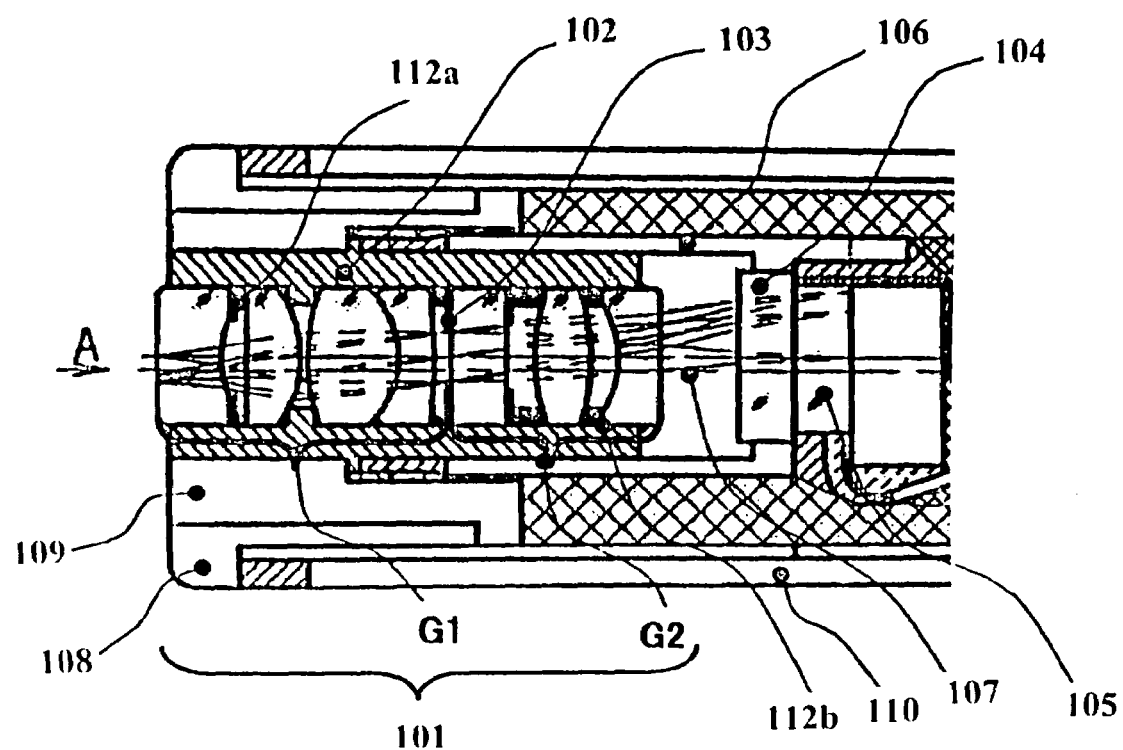
FIGS. 11(*a*) and 11(*b*) are a cross-sectional view and an end view, respectively, of the magnifying image pickup unit of Embodiment 1.
Figure 11B:
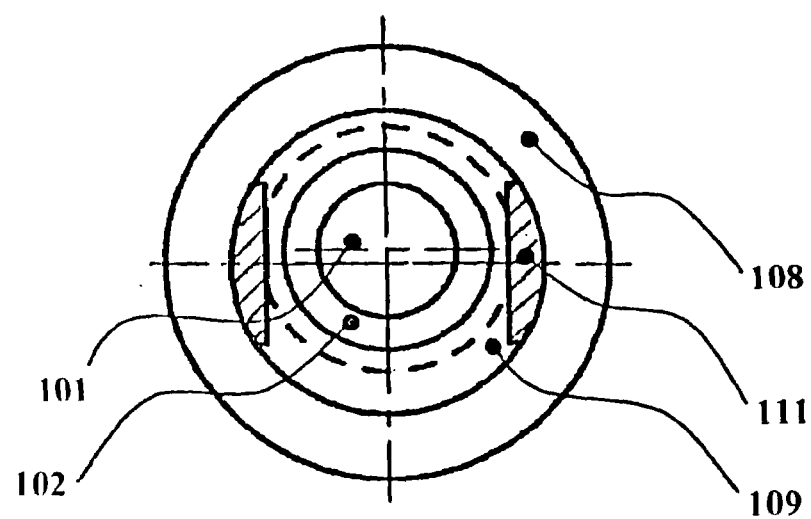

FIG. 11(b) is an end view looking in the direction indicated by the arrow A in FIG. 11(a). The intermediate member 109 has cutouts (indicated by cross-hatching) at its periphery through which an illumination fiber 111 may be inserted and affixed thereto. After the intermediate member 109 and illumination fiber are affixed to the hard tip member 108, the image pickup unit is inserted and affixed to the intermediate member 109.

Referring to FIG. 11(a), when adjustment is required, for example, in the absolute value of the image scale factor, the gaps 112a and 112b that are provided before and after the aperture stop 103 can be adjusted to provide a larger or smaller space, if necessary. To do so, gap adjustment rings that are made of ultra-thin plates may be used for gap adjustment. A gap adjustment part is designed to hold a stack of such ultra-thin plates. A different number of ultra-thin plates may be used according to the varied gap sizes needed as a result of an assembly process in which parts having a variety of dimensional errors are used.

Table 1 below lists the surface number #, in order from the object side, the radius of curvature R (in mm) of each surface, the on-axis surface spacing D (in mm), as well as the refractive index Nd and the Abbe number υd (both at the d-line) of each optical element of Embodiment 1. Also listed is the outer lens diameter LD of each lens element of Embodiment 1. In the bottom portion of the Table are listed the distance to the object and the image height, in mm.

TABLE 1

| # | R | D | Nd | υd | LD |
|---|---|---|---|---|---|
| 1 | ∞ | 0.46 | 1.5183 | 64.14 | 1 |
| 2 | 0.84 | 0.17 | | | |
| 3 | ∞ | 0.4 | 1.7323 | 54.68 | 1 |
| 4 | −0.817 | 0.05 | | | |
| 5 | 1.353 | 0.65 | 1.7323 | 54.68 | 1 |
| 6 | −0.703 | 0.25 | 1.7044 | 30.131 | |
| 7 | −3.804 | 0.09 | | | |
| 8 | ∞(stop) | 0.03 | | | |
| 9 | ∞ | 0.4 | 1.5156 | 75.00 | 1 |
| 10 | ∞ | 0.2 | | | |
| 11 | 1.566 | 0.4 | 1.67 | 48.32 | 1 |
| 12 | −1.566 | 0.2 | | | |
| 13 | −0.729 | 0.3 | 1.5198 | 52.43 | 1 |
| 14 | ∞ | 0.56 | | | |
| 15 | ∞ | 0.4 | 1.5183 | 64.14 | |
| 16 | ∞ | 0.01 | 1.5119 | 63.00 | |
| 17 | ∞ | 0.4 | 1.6138 | 50.20 | |
| 18 | ∞ | 0.01 | 1.5220 | 63.00 | |
| 19 | ∞ | 0 | | | |

Distance to the object = 0
Image height = 0.500

EMBODIMENT 2

Figure 12A:
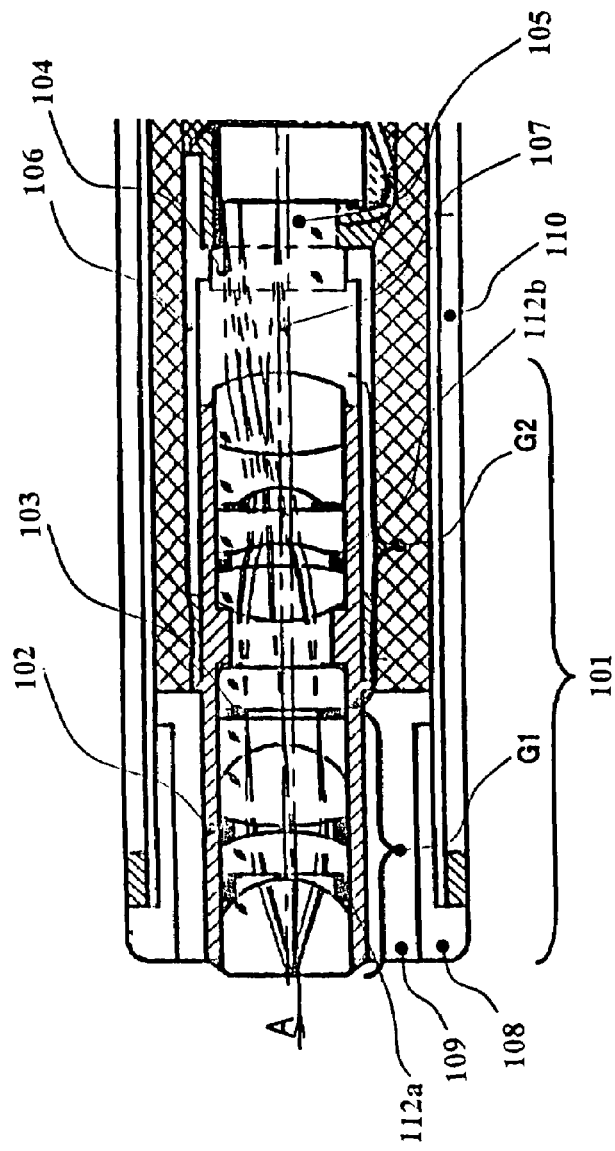
FIGS. 12(*a*) and 12(*b*) are a cross-sectional view and an end view, respectively, of the magnifying image pickup unit of Embodiment 2.
Figure 12B:
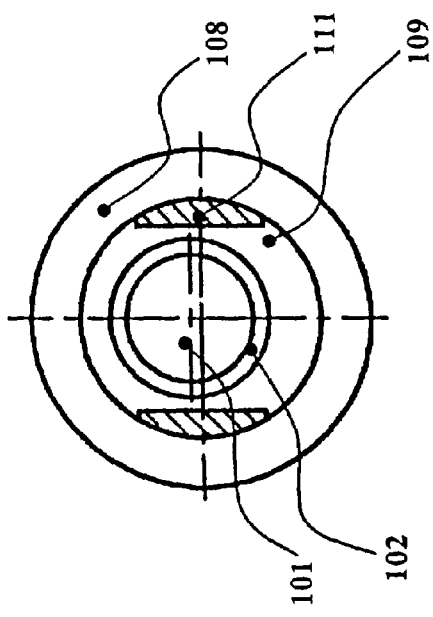

FIG. 12(*a*) is a side cross section of the magnifying image pickup unit of Embodiment 2, and FIG. 12(*b*) shows an end view looking in the direction of the arrow A shown in FIG. 12(*a*).

Table 2 below lists the surface number #, in order from the object side, the radius of curvature R (in mm) of each surface, the on-axis surface spacing D (in mm), as well as the refractive index Nd, and the Abbe number υd (both at the d-line) of each optical element for Embodiment 2. Also listed is the outer lens diameter LD of each lens element of Embodiment 2. In the bottom portion of the Table are listed the distance to the object and the image height, in mm.

TABLE 2

| # | R | D | Nd | υd | LD |
|---|---|---|---|---|---|
| 1 | ∞ | 0.88 | 1.8882 | 40.76 | 1.2 |
| 2 | −0.703 | 0.05 | | | |
| 3 | ∞ | 0.4 | 1.5183 | 64.14 | 1.2 |

TABLE 2-continued

| # | R | D | Nd | υd | LD |
|---|---|---|---|---|---|
| 4 | −1.485 | 0.05 | | | |
| 5 | 2.085 | 0.76 | 1.8081 | 46.57 | 1.2 |
| 6 | −0.703 | 0.25 | 1.8126 | 25.42 | 1.2 |
| 7 | ∞ | 0.05 | | | |
| 8 | ∞(stop) | 0.03 | | | |
| 9 | ∞ | 0.4 | 1.5156 | 75.00 | 1.2 |
| 10 | ∞ | 0.43 | | | |
| 11 | 1.131 | 0.5 | 1.8395 | 42.72 | 1.2 |
| 12 | −3.127 | 0.2 | | | |
| 13 | −1.061 | 0.3 | 1.8126 | 25.42 | 1.2 |
| 14 | ∞ | 0.2 | | | |
| 15 | −0.592 | 0.3 | 1.8081 | 46.57 | 1.2 |
| 16 | 2.132 | 0.77 | 1.8126 | 25.42 | 1.2 |
| 17 | −1.262 | 0.77 | | | |
| 18 | ∞ | 0.4 | 1.5183 | 64.14 | |
| 19 | ∞ | 0.01 | 1.5119 | 63.00 | |
| 20 | ∞ | 0.4 | 1.6138 | 50.20 | |
| 21 | ∞ | 0.01 | 1.5220 | 63.00 | |
| 22 | ∞ | 0 | | | |

Distance to the object = 0
Image height = 0.500

Table 3 below lists the values of the variables of interest for Embodiments 1 and 2.

TABLE 3

| item | legend | unit | Embodiment 1 | Embodiment 2 |
|---|---|---|---|---|
| image scale factor | βo | | −2.678847 | −6.63 |
| focal length of front lens group | f1 | [mm] | 0.765 | 0.591 |
| focal length of rear lens group | f2 | [mm] | 3.476 | 4.557 |
| focal length | f | [mm] | 0.657 | 0.797 |
| half of field angle | wy | [deg] | 6.141 | 3.95 |
| exit angle of chief ray | wy' | [deg] | 13.965 | 6.02 |
| numerical aperture on the object side | NA | | 0.2184 | 0.55 |
| stop diameter | Φ1 | [mm] | 0.36 | 0.66 |
| largest lens diameter | Φ2 | [mm] | 1 | 1.2 |
| pitch | P | [µm] | 4 | 4 |
| reference wavelength | λ | [µm] | 0.546 | 0.546 |

Table 4 below lists the Conditions (1)-(6) and the values corresponding thereto for Embodiments 1 and 2.

TABLE 4

| Condition No. | Condition | Embodiment 1 | Embodiment 2 |
|---|---|---|---|
| 1 | $1 < |\beta o| \leq 10$ | 2.680 | 6.630 |
| 2 | $0.9 \leq |\cos wy'/\cos wy| \leq 1.1$ | 0.976 | 0.997 |
| 3 | $0.1 \leq NA \leq 0.8$ | 0.220 | 0.550 |
| 4 | $0.1 \leq |p \cdot NA^2/(0.61 \cdot \lambda \cdot \beta o)| \leq 0.8$ | 0.215 | 0.544 |
| 5 | $0.2 \leq \Phi 1/(\Phi 2 \cdot f) \leq 2$ | 0.471 | 0.931 |
| 6 | $2 \leq f2/f1 \leq 10$ | 4.544 | 7.711 |

A video observation system suitable for in vivo cellular observation will now be described. As mentioned above, living tissues of interest often include parenchymal tissues with transparent epithelial cells overlying the parenchymal tissues. The following techniques are used in order to create sufficient contrast between the cell nuclei and other cell portions so as to enable observation of the epithelial cells within a targeted observation region with no interference from the underlying parenchymal tissues. For example, a video observation system suitable for distinctly observing a layer of cells that have been stained blue for improved contrast has the following configuration.

Figure 3:
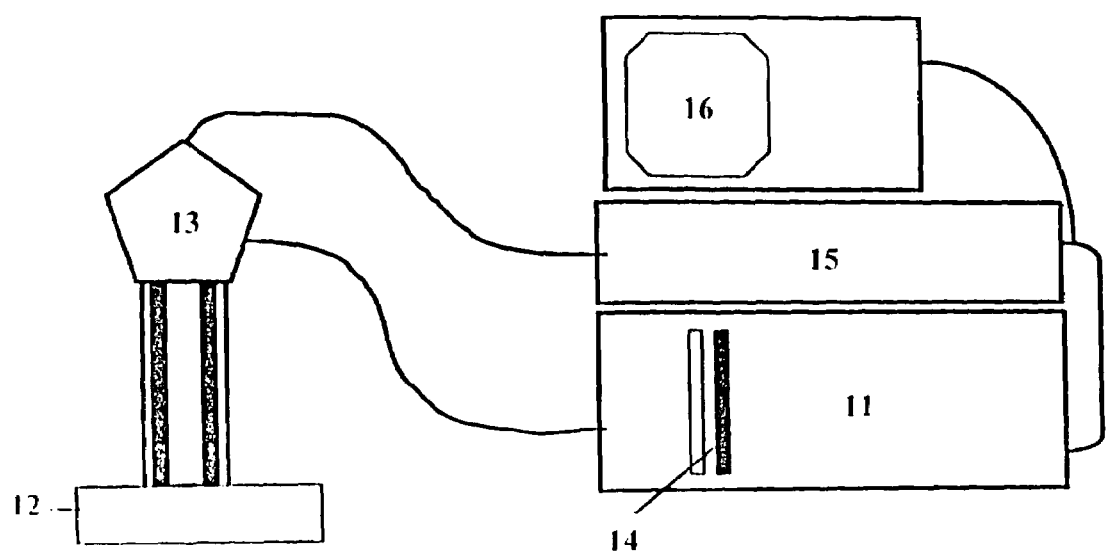
FIG. 3 shows a configuration of a magnifying image pickup unit according to the present invention, along with other components for displaying endoscopic images.

FIG. 3 shows a configuration for the video observation system that uses the magnifying image pickup unit of the present invention. The illumination light supplied by a light source device 11 illuminates an object 12 via a magnifying image pickup unit 13. The light source device 11 is provided with a wavelength selection filter 14, which is positioned in the illumination light path, as required, to produce illumination light having a wavelength profile suitable for cellular observation. When illumination light having a visible wavelength range is used to illuminate living tissue, the shorter wavelengths that correspond to blue reach only the surface of tie living tissue. These wavelengths are useful to obtain information specific to the epithelial cells of the living tissue. Light having wavelengths around 500 nm (corresponding to the color green) reaches only slightly below the surface of living tissue. On the other hand, light wavelengths corresponding to the color red reach relatively deep inside living tissue.

An image is formed by the objective optical system of the magnifying image pickup unit 13 at the image pickup surface of the image pickup element. The image pickup unit converts the image into electrical signals and sends them to an image processing unit 15. In processing image data of the visible region, green wavelength components are used to produce the brightness information of the object. In this way, images are obtained that are similar to those acquired through the human eye. The image data that are processed by the image processing unit 15 are displayed oil a TV monitor 16.

Figure 4:
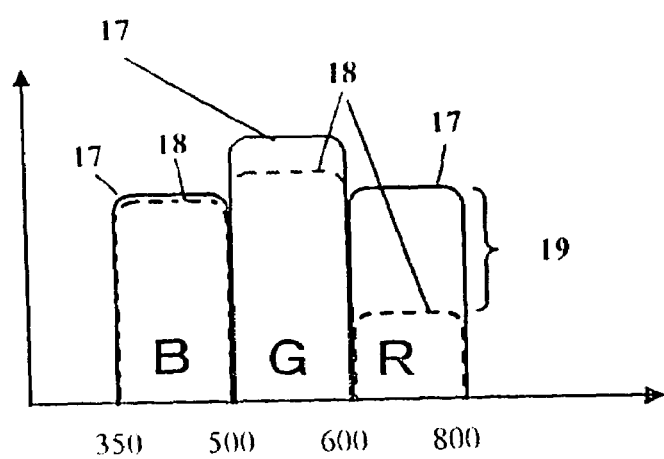
FIG. 4 shows the spectral wavelength distribution of an image detected by an image pickup unit according to the present invention.

When the cells that have been stained blue are illuminated by white light that equally contains blue, green, anal red components, the portions that have been stained blue appear blue while unstained portions appear white. FIG. 4 shows a wavelength profile of a cellular image formed by the magnifying image pickup unit, with the Y-axis (the ordinate) being the light intensity in arbitrary units and the X-axis (the abscissa) being the wavelength in nm. Unstained portions do not absorb specific light wavelengths and thus provide a nearly flat wavelength profile, as is shown by the solid lines 17. Portions that have been stained blue absorb red light and give a wavelength profile with a drop in intensity primarily for the red component, as shown by the broken lines 18.

In this way, the contrast between the background (the unstained portions, shown by the solid lines) and the cell nuclei and walls (tile stained portions, shown by the broken lines) appears as a difference in light reflection 19 that is due to light absorption that occurs primarily at the longer wavelengths (i.e., the red component) for images obtained using the magnifying image pickup unit.

Figure 6:
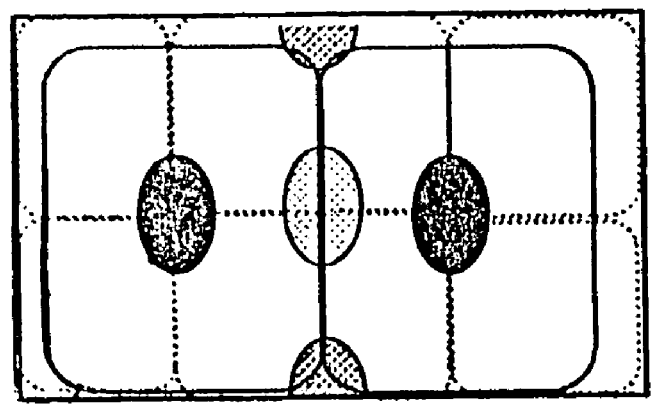
FIG. 6 shows the appearance of cells in the background that overlap cells of interest in the foreground.

As shown in FIG. 1, the epithelial cells are vertically layered. When observing the cells in a specific layer, the images of layers of cells that are not at the depth of interest in the epithelial cells and the cells of the underlying parenchymal tissues overlap in the background, thereby reducing the image contrast. Cell walls are only slightly stained by the staining processes as compared to cell nuclei. FIG. 6 illustrates the situation where the images of cells that are not of interest overlap in the background, and the cell walls are barely recognizable.

In order to climinate unwanted images (i.e., noise) overlapping in the background, the light that transmits information about the parenchymal tissues, and the cell layers that are not at the depth of interest can be cut off in the illumination light path or in the objective optical system before the light is detected by the image pickup element. In this embodiment of the video observation system, a filter for cutting off a specific range of wavelengths is inserted in the illumination light path in order to eliminate unnecessary wavelength components from the illumination light. In this case, unnecessary components are mainly the longer wavelengths of the visible light range, such as red light. However, it is not desirable to eliminate all the red light components because this cuts off the wavelength components that serve to provide contrast between the portions that have been stained blue and the unstained portions.

Figure 7:
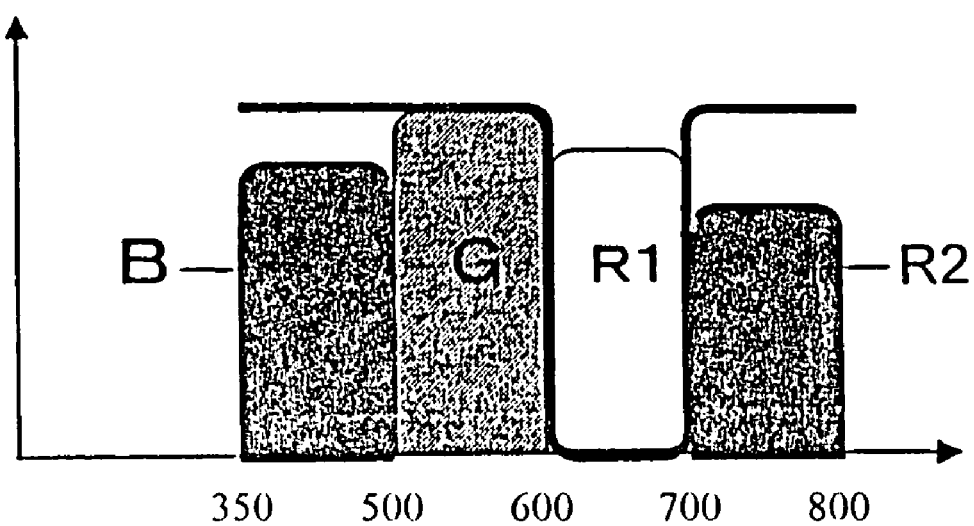
FIG. 7 shows the spectral transmittance of a wavelength selection filter used in an embodiment of the present invention.
Figure 8:
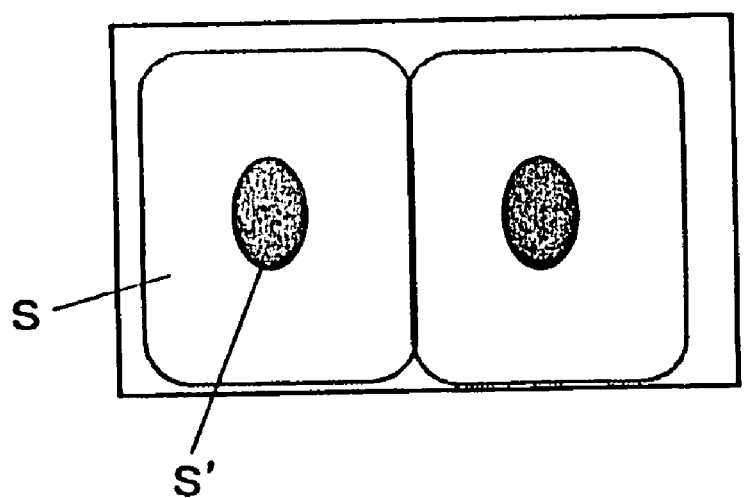
FIG. 8 shows an image in which information from regions other than regions at a desired depth is eliminated.

The present invention uses, for the wavelength selection filter 14 of the light source, a filter having a spectral transmittance as shown in FIG. 7. FIG. 7 shows the spectral transmittance by solid line with the ordinate (i.e, the Y-axis) being the transmittance and the abscissa (i.e., the X-axis) being the wavelength in nm. More specifically, among the illumination light that includes the blue, green, and red wavelength ranges, the illumination light of the red wavelength range is divided into two wavelength bands R1 and R2. Among the wavelength bands R1 and R2, the wavelength band R1 that is nearer the green wavelength range is cut off by the filter and thus prevented from illuminating the object. The wavelength band R1 may be, for example, the range 600 nm<λ<700 nm, and the wavelength band R2 may be, for example, tile range 700 nm<λ<800 nm. FIG. 8 shows an image in which information from regions other than regions at a desired depth is eliminated.

Using illumination light with the wavelength band R1 cut off allows limited light to reach the parenchymal tissues and the cell layers that are not at the depth of interest, but are within the depth of field of the objective optical system. Thus, the image resolution in the depth direction is improved by preventing overlapping of unwanted images. On the other hand, the light in the wavelength band R2 contributes to producing contrast between the cell nuclei that have been stained blue verses the cell walls and other cell portions that remain relatively unstained. Thus, a clear image of the cell layer of interest is obtained with the information from unnecessary depths being eliminated. The transmittance characteristic shown in FIG. 7 can be realized using a dichroic filter.

A contrast medium can be used to enhance only the cell nuclei. In such a case, the contrast medium that is absorbed by the cell nuclei has outer electrons that are excited by excitation light and which emit fluorescent light when they return to the ground state. This fluorescent light can be observed in order to accurately identify the cell nuclei. In particular, the video observation system according to the present invention is useful for a method where a gene contrast medium, such as a gene marker (for example GFP) that reacts with light, can be injected into the cells and the identification of a specific gene that occurs when healthy cells are transformed into diseased cells such as cancer may be accomplished.

In the method above, the gene in a living cell is altered immediately before the onset of disease and a gene marker, which takes no action among the normal cells, identifies diseased areas and emits weak fluorescence in response to excitation light. Thus, the video observation system used for this observation is desirably provided with a hypersensitive camera.

Figure 15:
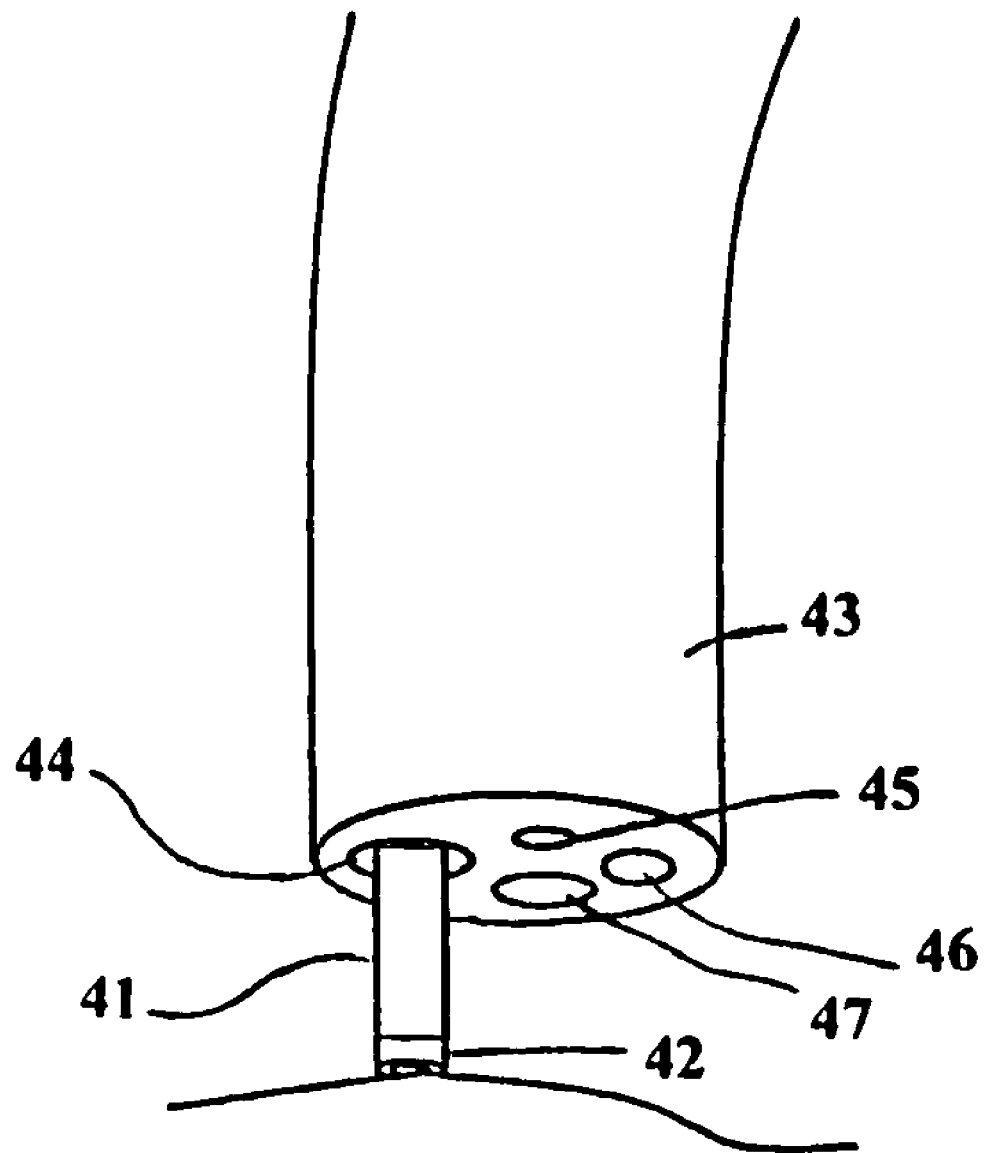
FIG. 15 shows an image pickup unit that simultaneously displays both conventional endoscope images and fluorescent images for observation of cell nuclei.

It is preferable that the video observation system for fluorescent image observation of cell nuclei be used in combination with a conventional endoscope. FIG. 15 shows an example of such a combination. The fluorescent image observation system is formed as a thin endoscope that has all elongated portion 41. A magnifying image pickup unit 42 of the fluorescent image observation system is mounted on the distal end of the elongated portion. The reference numeral 43 denotes a conventional endoscope that has a channel 44 that extends from the distal end to the proximal end (not shown) of the conventional endoscope. The conventional endoscope also has an observation window 45 as well as illumination windows 46 and 47 at its distal end. The channel is also used for inserting treatment tools. The elongated portion 41 of the fluorescent image observation system is inserted into the channel 44 from the proximal end of the conventional endoscope 43 and comes out of the channel 44 via the opening in the channel. The endoscope observation system is inserted into a body cavity to be observed. The conventional endoscope provides images of the elongated portion 41 that protrudes from the channel for guiding the magnifying image pickup unit 42 to the targeted observation region. The TV monitor 16 (shown in FIG. 3) displays images from the conventional endoscope as well as fluorescent images from the image pickup unit simultaneously, thereby providing more precise and accurate observations.

Figure 9:
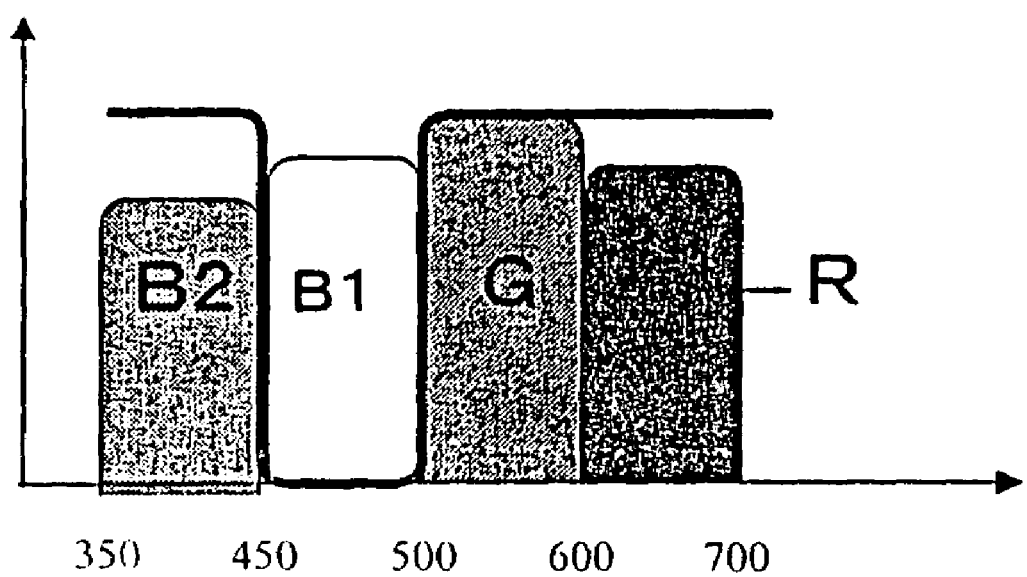
FIG. 9 shows the spectral transmittance of another wavelength selection filter used in an embodiment of the present invention.

When a contrast medium that primarily absorbs light of wavelengths shorter than 480 nm and emits fluorescent light having wavelengths longer than 470 nm is used, a preferred wavelength selection filter 14 for the light source has a spectral transmittance as shown in FIG. 9. In FIG. 9, the spectral transmittance is shown by the solid lines with the ordinate illustrating the transmittance and the abscissa being the wavelength in nm.

More specifically, the illumination light of the blue wavelength range is divided into two wavelength bands B1 and B2 and, among the wavelength bands B1 and B2, the wavelength band B1 that is nearer the green wavelength range is cut off by the filter. For example, the wavelength band B1 may lie in the range 450 nm<$\lambda$<500 nm and the wavelength band B2 may lie in the range 350 nm<$\lambda$<450 nm. In such a case, the objective optical system may be provided with a filter that transmits light having wavelengths longer than about 470 nm and cuts off light having wavelengths shorter than about 470 nm. Thus, fluorescent images can be observed while the excitation light is cut off. The light of the wavelength band B1 that includes the excitation and fluorescent wavelengths is cut off from the illumination light. This enables clear images using weak fluorescence to be observed with no interference from the excitation light.

The wavelength selection filter 14 for the light source device can be used with a filter that reduces the light intensity of either the green or red wavelength range. This prevents unnecessary image noise in the background of fluorescent images of the cell nuclei and allows a conventional endoscope to produce conventional observation images of living tissue.

Figure 13:
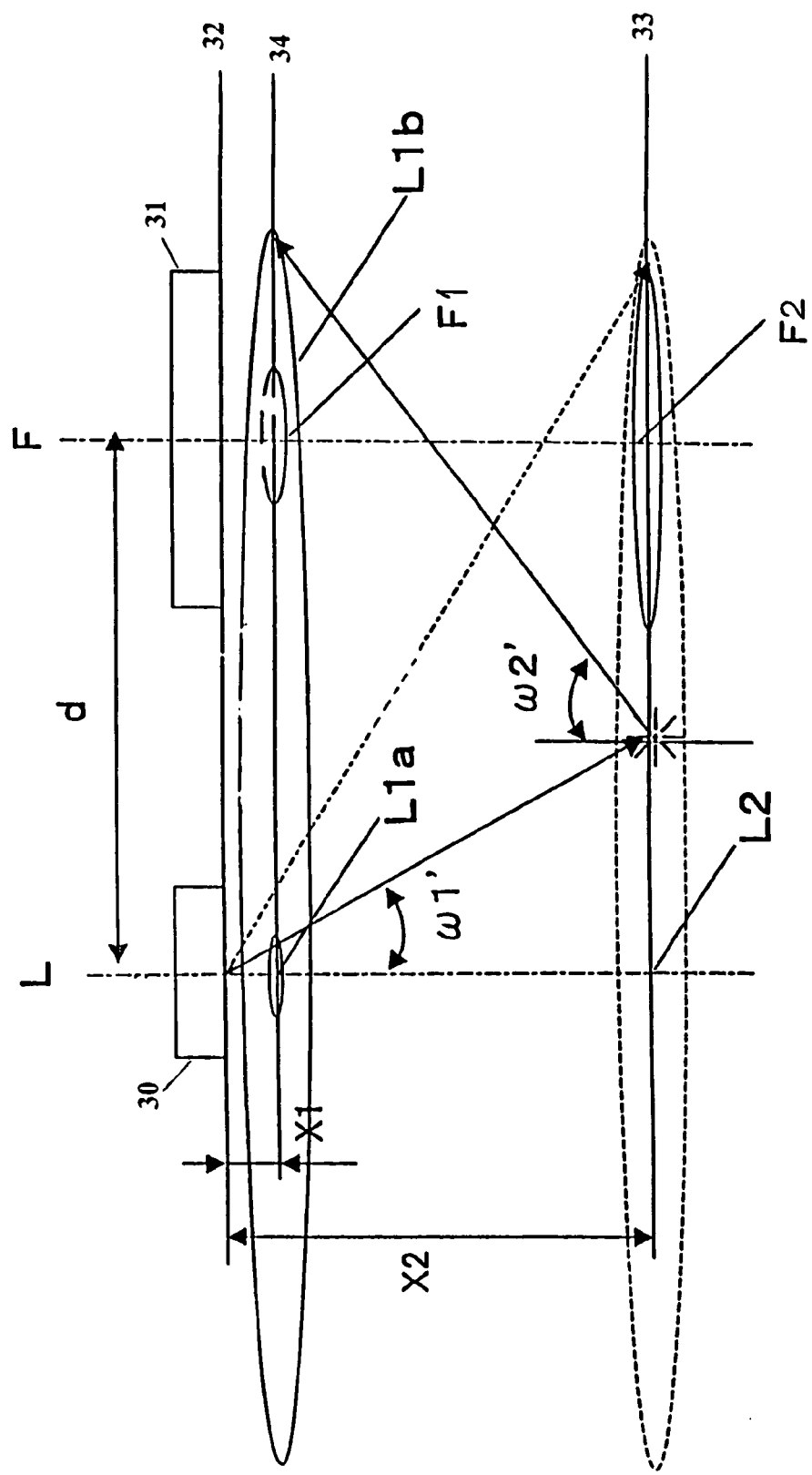
FIG. 13 illustrates an illumination method suitable for in vivo cellular observation.

An illumination method suitable for in vivo cellular observation is described hereafter with reference to FIG. 13. The tip of an illumination unit 30 that serves to illuminate an object and the tip of an objective optical system 31 that serves to form images on the image pickup surface of an image pickup element using light from the object are located at the tip 32 of an endoscope. The central axis L of the illumination field of the illumination unit 30 is substantially parallel to and shifted from the central axis F of the field of view of the objective optical system 31 by a distance d; thus, the center line of the illumination field and the center line of the objective optical system (i.e., of the observation field) are directed in substantially the same direction. The endoscope tip 32 is placed adjacent living tissue in order to observe the living tissue. The distance between a targeted region of the living tissue and the endoscope tip is adjusted so that the targeted region among the epithelial cells and parenchyrnal tissues which form the living tissue is "in-focus" (i.e., centrally located within the depth of field of the objective optical system). As shown in FIG. 13, the distance between the position of the epithelial cells 34 and endoscope tip 32 is X1 and the distance between the position of the parenchymal tissues 33 and the endoscope tip 32 is X2.

The conventional endoscope uses the field of view F2 of the objective optical system to observe the parenchymal tissues at the distance of X2. The distance d between the central axis L of the illumination field and the central axis F of the field of view at the endoscope tip is determined in a manner such that the illumination field L2, which is positioned in front of the endoscope tip by a distance X2, includes the field of view F2 in order to ensure a uniform brightness in the field of view F2. The distance X2 is several millimeters to several tens of millimeters.

On the other hand, the magnifying endoscope uses an objective optical system having a field of view F1 in order to observe the epithelial cells at a distance X1. The distance X1 is within the range of zero to several microns, that is, substantially zero. Therefore, as shown in FIG. 13, the illumination field L1a, which is positioned in front of the endoscope tip by the distance X1, may fail to include the field of view F1 of the magnifying endoscope even when the distance d between the central axes of the illumination field L and the field of view F at the endoscope tip is reduced. Consequently, it is understood that the conventional illumination method fails to ensure a uniform brightness in the field of view F1 of the objective optical system. The present invention provides an illumination method in which the parenchymal tissues that are positioned still farther in front of the endoscope tip than the farthest position of the depth of field of the objective optical system are utilized for uniformly illuminating the field of view F1 of the objective optical system.

As shown in FIG. 13, an observation target is at a distance X1 from the endoscope tip 32 and the parenchymal tissues 33 are at a distance of X2 from the endoscope tip. The illumination light emitted from the endoscope tip 32 reaches the parenchymal tissues via the illumination field L1a. The parenchymal tissues 33 serve as reflecting and scattering surfaces and thus scatter the illumination light. It is assumed that the illumination light emitted from the endoscope tip 32 has a Gaussian light distribution profile, and the effective light distribution angle of illumination will herein be defined as a light distribution angle $\omega$ that provides a light intensity that is 1/e times the light intensity on-axis, where e is the base of the natural logarithm.

As shown in FIG. 13, the illumination light emitted from the endoscope tip 32 is transmitted through the living tissues at the light distribution angle $\omega 1'$ before it reaches the parenchymal tissues 33. After being reflected and scattered by the parenchymal tissues, the illumination light is emitted at the light distribution angle $\omega 2'$ and thereafter it reaches the epithelial cells at the in-focus region 34 and forms the illumination field L1b at a distance X1 from the endoscope tip that includes the field of view F1 of the objective optical system. Consequently, uniform brightness is ensured in the field of view F1 of the objective optical system. Thus, an object placed in contact with a distal end of the observation unit so that a light source that does not directly illuminate an observation field of view illuminates an area of tissue outside the observation field of view, and the illuminated tissue scatters light from the light source so as to illuminate the observation field of view. The observation unit is then used to observe an image of the observation field with a scale factor larger than 1.

The light distribution angles ω1' and ω2' are light distribution angles within living tissues. The following Equations (B) and (C) are used to convert these light distribution angles to the equivalent light distribution angles ω1, ω2 in air.

$$\sin \omega1 = 1.33 \cdot \sin \omega1' \qquad \text{Equation (B)}$$

$$\sin \omega2 = 1.33 \cdot \sin \omega2' \qquad \text{Equation (C)}$$

The parenchymal tissues are outside the depth of field of the objective optical system, therefore, the light reflected and scattered by the parenchymal tissues is not imaged and thus merely the illumination effect on the epithelial cells is obtained. It is preferred that the distance d at the endoscope tip between the central axes of the illumination field L and the field of view F satisfies the following Condition (7):

$$1 \leq \log(d/(X1 \cdot \tan \omega)) \leq 3 \qquad \text{Condition (7)}$$

where d is the distance between the central axis of the illumination field and the central axis of the field of view of the objective optical system, X1 is the distance between the leading surface of the endoscope (i.e., the endoscope tip) and the in-focus point of the objective optical system, and ω is the light distribution angle that provides a light intensity that is 1/e times the light intensity on-axis, where e is the base of the natural logarithm.

When the upper limit of Condition (7) is not satisfied, uniform brightness will not be ensured in the field of view of the objective optical system. When the lower limit of Condition (7) is not satisfied, it will be difficult to locate the tips of the illumination unit and the objective optical system at the endoscope tip with the outer diameter of the endoscope tip being maintained small.

In addition, the following Condition (8) is preferably satisfied:

$$5 \leq d/(X2 \cdot \tan \omega) \leq 30 \qquad \text{Condition (8)}$$

where d and ω are as defined above, and

X2 is the distance between the leading surface of the endoscope (i.e., the endoscope tip) and the reflecting and scattering surfaces, such as the parenchymal tissues.

When the upper and lower limits of Condition (8) are not satisfied, uniform brightness will not be ensured in the field of view of the objective optical system.

It is also preferred that the following Condition (9) be satisfied:

$$0.5 \leq \log (X2/X1) \qquad \text{Condition (9)}$$

where

X2 and X1 are as defined above.

When Condition (9) is not satisfied, the parenchymal tissues are imaged in the field of view, deteriorating the image quality.

Table 5 below lists various values of X2, X1, d and ω pertaining to Embodiments 1 and 2 of the present invention.

TABLE 5

| item | legend | unit | Embodiment 1 | Embodiment 2 |
|---|---|---|---|---|
| scatterer distance | X2 | [mm] | 0.1 | 0.1 |
| objective in-focus distance | X1 | [mm] | 0.015 | 0.002 |
| illumination parallax | d | [mm] | 0.8 | 1 |
| illumination distribution angle | ω | [deg] | 35 | 35 |

Table 6 below lists the Conditions (7)-(9) and the value of each for Embodiments 1 and 2.

TABLE 6

| Condition No. | Condition | Embodiment 1 | Embodiment 2 |
|---|---|---|---|
| 7 | 1 ≤ log (d/(X1 · tan ω)) ≤ 3 | 1.88 | 2.85 |
| 8 | 5 ≤ d/(X2 · tan ω) ≤ 30 | 11.4 | 14.3 |
| 9 | 0.5 ≤ log (X2/X1) | 0.82 | 1.7 |

The method for diagnosing the presence/absence of abnormal cells (i.e., whether cells are cancerous or not) from magnified cell images will now be described.

Figure 5:
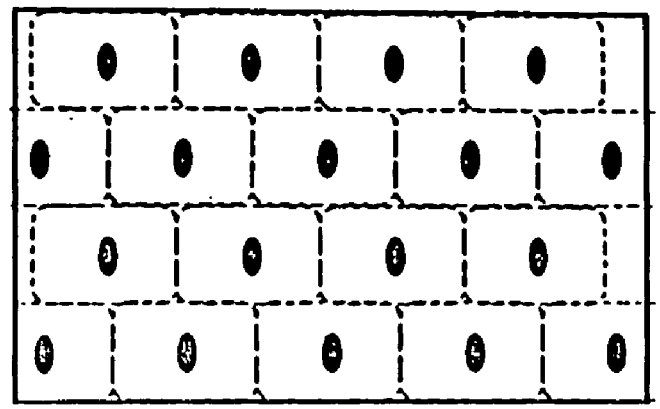
FIG. 5 shows a magnified image of cells that have been stained for observation according to an embodiment of the present invention.

FIG. 5 shows stained cells that are magnified and observed according to Embodiment 1. The image pickup unit used in the magnifying endoscope observation system is set for a scale factor that allows several tens to several hundreds of nuclei to be observed on a monitor. For example, several tens to several hundreds of cell nuclei are displayed on a monitor and the cell density in the observation field of view can be evaluated based on the distance between cell nuclei in order to diagnose the presence/absence of abnormal cells. The cell density can be compared with normal samples and statistically analyzed.

The magnifying endoscope observation system above is specified for a resolution and a magnification sufficient for nucleic observation. With the observation scale factor further increased, the image pickup unit displays several cell nuclei on a monitor and the number of cell nuclei in a unit area is translated to the cell size, or the cell nuclei are evaluated for shape, in order to diagnose the presence/absence of abnormal cells. For example, cancerous cells present particular characteristics such as increased size and irregular shapes. Thus, the size and shape of cell nuclei can be evaluated in order to diagnose cancerous cells.

FIG. 8 shows cell nuclei and cell walls that are magnified and observed according to Embodiment 2 of the present invention. The magnifying endoscope observation system is set for a scale factor that allows several nuclei to be observed on a monitor. The ratio of the area S' of the cell nuclei divided by the area S within the cell walls in the field of view is herein defined as the "occupancy" of the nuclei in the cells, and is used to diagnose the presence/absence of abnormal cells. For this analysis, the magnifying endoscope observation system is specified so as to have a resolution and contrast sufficient for observation of both cell nuclei and cell walls.

Figure 14:
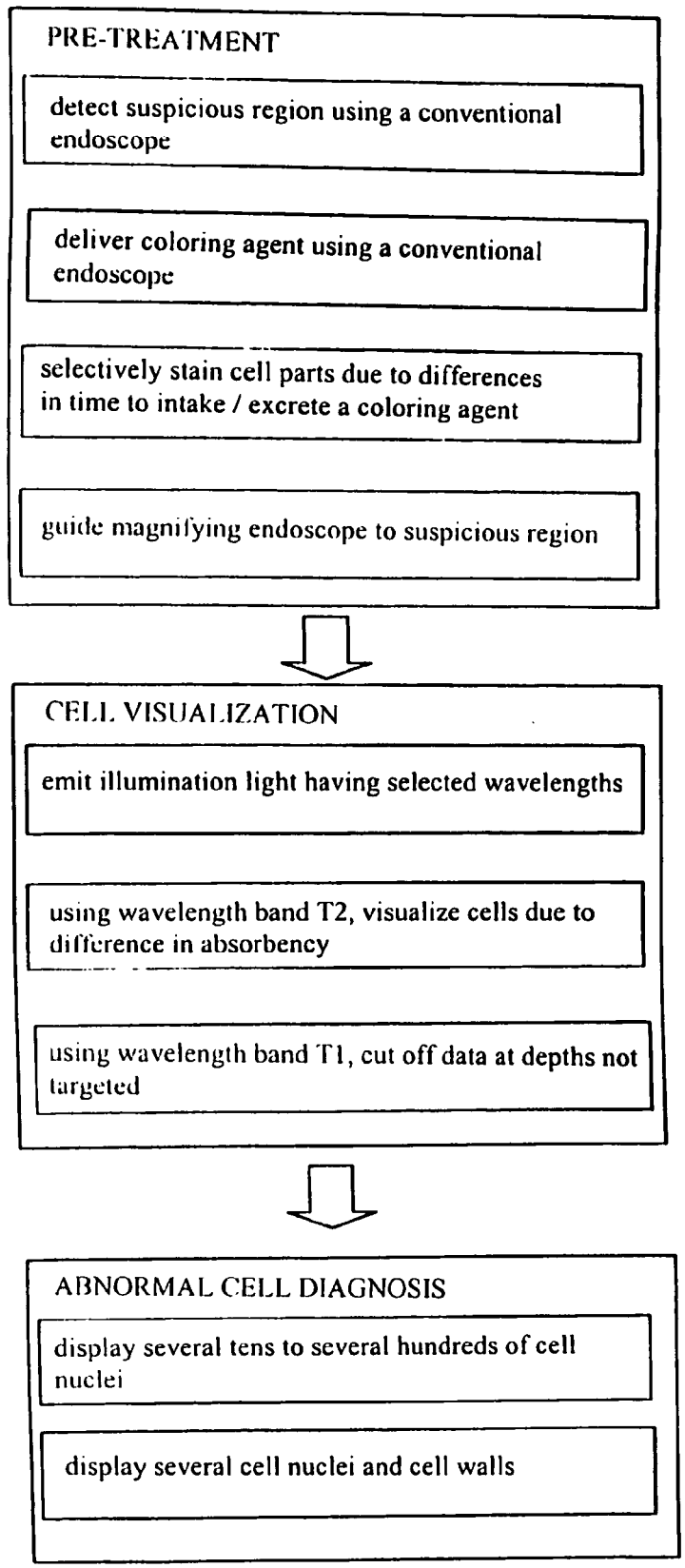
FIG. 14 is a flow chart of the steps for in vivo cellular observation according to the present invention.

FIG. 14 is a flow chart of a series of procedures for the in vivo cellular observation described above. As noted in the drawing, there is a pre-treatment stage, followed by a cell visualization stage, followed by a stage of abnormal cell diagnosis. During pre-treatment, the following steps are preformed: detect a suspicious region by using a conventional endoscope; deliver a coloring agent using a conventional endoscope; selectively stain cell parts due to differences in time for cells to intake or excrete the coloring agent; and guide a magnifying endoscope to the suspicious region and contact the tip thereof to the region for observation. During cell visualization the following step is performed: emit illumination light having selected wavelengths; the illumination light including wavelength band T2, with the wavelength band T1 being nearer the green wavelength range than is the wavelength band T2, for visualizing cells due to differences in absorbency, and wavelength band T1 for cutting off data at depths not targeted. During abnormal cell diagnosis, the following steps are performed: display several tens to several hundreds of cell nuclei; and, display several cell nuclei and the cell walls. Note that in CELL VISUALIZATION of FIG. 14, the second and third boxes are not separate steps; instead, these boxes merely indicate the details of the selected wavelengths.

The system described above in which specific wavelength bands are used from a white light source provides excellent flexibility where plural wavelength properties are selectively used in the illumination light, depending on the observation target and the selected coloring agent. On the other hand, where the wavelength property of the illumination light is predetermined, a single color illumination light, for example, can be used to further simplify the configuration.

Figure 10B:
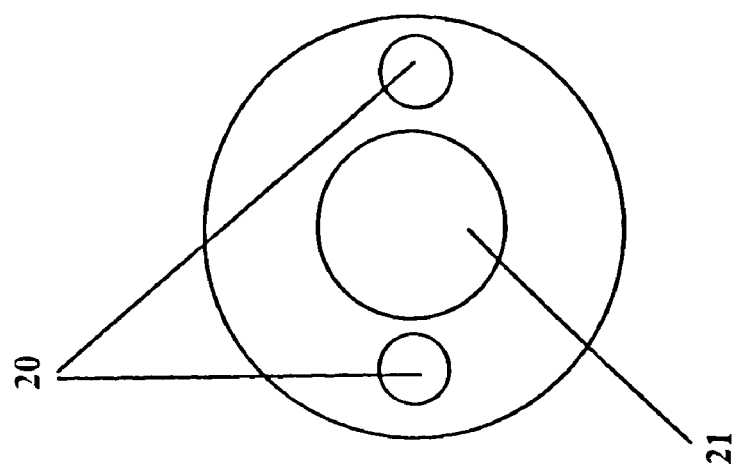
FIGS. 10(*a*) and 10(*b*) are a side cross section and an end view, respectively, of an insert tip part of an endoscope imaging system that uses specific wavelengths for observation.
Figure 10A:
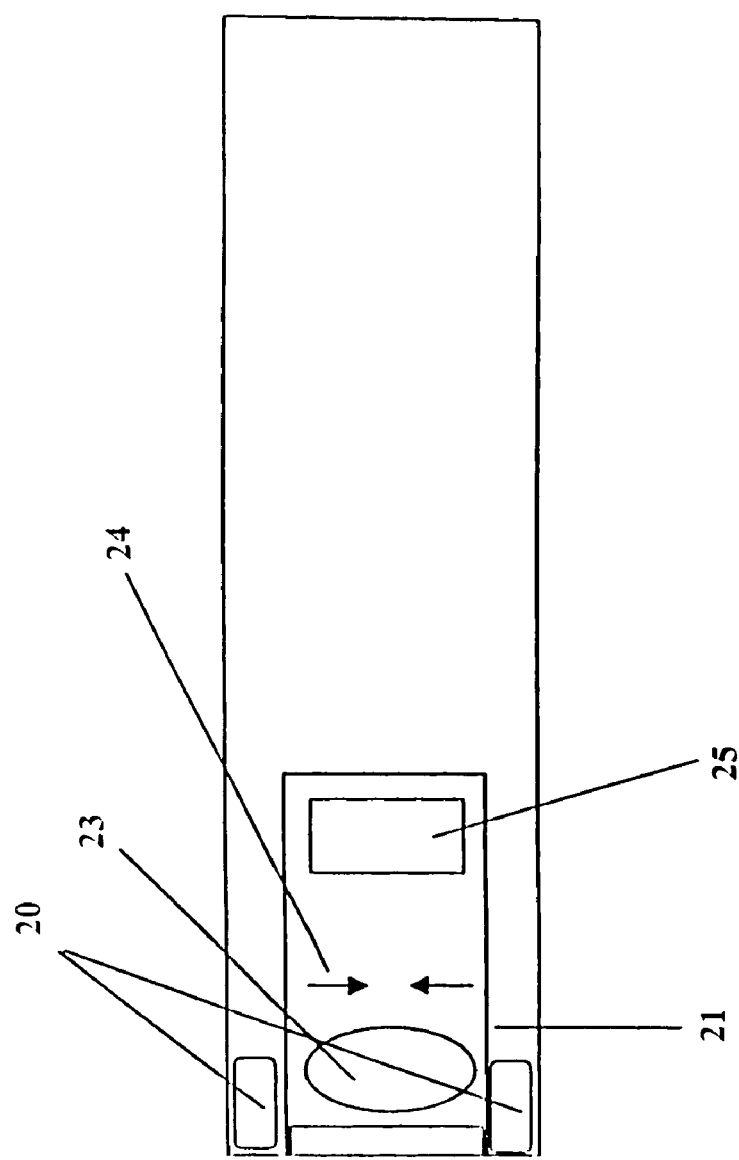

An endoscope tip part of an endoscope imaging system specified for observation with specific wavelengths of light is illustrated in FIGS. 10(a) and 10(b), with FIG. 10(a) being a side cross section and FIG. 10(b) being an end view. The image pickup unit according to the present invention has a small observation distance and therefore, the light source can be formed of LEDs 20 that emit a single color at low power. The LEDs 20 can be mounted in the endoscope body. Furthermore, when LEDs are installed at the tip of the endoscope, a light transmission optical fiber can be eliminated. Because aberration correction is necessary for only a single color when an LED light source is used, the fluorescent image observation system 21 can be provided with a simplified optical system that includes, for example, a single aspherical lens 23 positioned in front of a stop 24, and an image pickup element 25 positioned after the stop 24 at the image surface. Alternatively, plural spherical lenses (not shown) can be used in lieu of using a single aspherical lens.

An image pickup element that has been made compact and simplified as described above provides more freedom in mounting such an image pickup unit on a medical device such as an endoscope. For example, an image pickup unit may be combined with a treatment tool such as a catheter or laser probe that uses a flexible, insertable device. Or, an image pickup unit may be combined with a non-flexible treatment tool by making the image pickup unit compact and with a shape such as a pen or capsule by using wireless transmission of image data.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An endoscope comprising:
   an observation unit; and
   an illumination unit that illuminates an illumination field; wherein
   the observation unit includes an objective optical system having an observation field of view and an in-focus position;
   the observation field of view of the objective optical system at the in-focus position of the objective optical system does not overlap said illumination field; and
   a center line of the illumination field and a center line of the observation field are directed in substantially the same direction.

2. An endoscope comprising:
   an image pickup unit having an observation field of view, the image pickup unit including an objective optical system that forms a magnified image of an object in the observation field of view such that the absolute value of the image scale factor is larger than 1; and
   an illumination unit; wherein
   the image pickup unit and the illumination unit are positioned so that the observation field of view of the image pickup unit at the in-focus position does not overlap the illumination field of the illumination unit, and
   a center line of the illumination field and a center line of the observation field are directed in substantially the same direction.

3. An endoscopic observation method using an illumination unit and an observation unit comprising:
   illuminating an object placed in contact with a distal end of the observation unit so that a light source that does not directly illuminate an observation field of view illuminates an area of tissue outside the observation field of view, said area of tissue scatters light from the light source so as to illuminate the observation field of view; and
   observing an image of the observation field of view by the observation unit such that the absolute value of the image scale factor is larger than 1.

4. A method for observing epithelial cells of living tissue using an endoscope that includes:
   an observation unit; and
   an illumination unit that illuminates an illumination field; wherein
   the observation unit includes an objective optical system having an observation field of view and an in-focus position; and
   the observation field of view of the objective optical system at the in-focus position of the objective optical system does not overlap said illumination field;
   said method comprising:
   a step in which the illumination light emitted from the illumination system is scattered and reflected by the parenchymal tissues underlying the epithelial cells so as to illuminate the epithelial cells.

5. The method according to claim 4, wherein the following conditions are satisfied:

$$1 < |\beta o| \leq 10$$

$$0.9 \leq |\cos wy'/\cos wy| \leq 1.1$$

where
   $\beta o$ is the image scale factor of the objective optical system,
   $wy'$ is the incident angle at which a chief ray corresponding to the largest field angle enters the image pickup surface, and
   $wy$ is the half-field angle.

6. A method for observing epithelial cells of living tissue using an endoscope that includes:

an image pickup unit having an observation field of view, the image pickup unit including an objective optical system that forms a magnified image of an object in the observation field of view such that the absolute value of the image scale factor is larger than 1; and an illumination unit; wherein the image pickup unit and the illumination unit are positioned so that the observation field of view of the image pickup unit at the in-focus position does not overlap the illumination field of the illumination unit;

said method comprising:

a step in which the illumination system of the endoscope illuminates the underlying parenchymal tissues of the epithelial cells; and a step in which the illumination light emitted from the illumination system is scattered and reflected by the parenchyrnal tissues underlying the epithelial cells to illuminate the epithelial cells.

7. The method according to claim 6, wherein the following conditions are satisfied:

$$1 < |\beta o| \leq 10$$

$$0.9 \leq |\cos wy'/\cos wy| \leq 1.1$$

where $\beta o$ is the image scale factor of the objective optical system, $wy'$ is the incident angle at which a chief ray corresponding to the largest field angle enters the image pickup surface, and $wy$ is the half-field angle.

8. An endoscope comprising:

an observation unit; and an illumination unit that illuminates an illumination field; wherein the observation unit includes an objective optical system having an observation field of view and an in-focus position; and the observation field of view of the objective optical system at the in-focus position of the objective optical system does not overlap said illumination field;

wherein the following conditions are satisfied $$1 < |\beta o| \leq 10$$

$$0.9 \leq |\cos wy'/\cos wy| \leq 1.1$$

where $\beta o$ is the image scale factor of the objective optical system, $wy'$ is the incident angle at which a chief ray corresponding to the largest field angle enters the image pickup surface, and $wy$ is the image half-field angle.

9. An endoscope comprising:

an image pickup unit having an observation field of view, the image pickup unit including an objective optical system that forms a magnified image of an object in the observation field of view such that the absolute value of the image scale factor is larger than 1; and an illumination unit; wherein the image pickup unit and the illumination unit are positioned so that the observation field of view of the image pickup unit at the in-focus position does not overlap the illumination field of the illumination unit; and the following conditions are satisfied $$1 < |\beta o| \leq 10$$

$$0.9 \leq |\cos wy'/\cos wy| \leq 1.1$$

where $\beta o$ is the image scale factor of the objective optical system, $wy'$ is the incident angle at which a chief ray corresponding to the largest field angle enters the image pickup surface, and $wy$ is the image half-field angle.

10. An endoscope comprising:

an observation unit; and an illumination unit that illuminates an illumination field; wherein the observation unit includes an objective optical system having an observation field of view and an in-focus position; and the observation field of view of the objective optical system at the in-focus position of the objective optical system does not overlap said illumination field; and the light scattered and/or reflected at the illumination field fully illuminates the observation field of view.

11. An endoscope comprising:

an image pickup unit having an observation field of view, the image pickup unit including an objective optical system that forms a magnified image of an object in the observation field of view such that the absolute value of the image scale factor is larger than 1; and an illumination unit; wherein the image pickup unit and the illumination unit are positioned so that the observation field of view of the image pickup unit at the in-focus position does not overlap the illumination field of the illumination unit, and the light scattered and/or reflected at the illumination field fully illuminates the observation field of view.

* * * * *